United States Patent [19]
Van Gemert et al.

[11] Patent Number: 4,612,038
[45] Date of Patent: Sep. 16, 1986

[54] HERBICIDALLY ACTIVE 3-OXADIAZOLYL-2-IMIDAZOLIDINONES

[75] Inventors: Barry Van Gemert, Massillon; Jerome M. Lavanish, Akron; James A. Schwindeman, Fairlawn, all of Ohio

[73] Assignee: PPG Industries, Inc., Pittsburgh, Pa.

[21] Appl. No.: 748,511

[22] Filed: Jun. 24, 1985

[51] Int. Cl.$^4$ .................. A01N 43/82; C07D 413/04
[52] U.S. Cl. ........................................ 71/92; 548/133
[58] Field of Search ........................... 548/133; 71/92

[56] References Cited

U.S. PATENT DOCUMENTS 4,426,527  1/1984  Lavanish et al. .................. 548/133

Primary Examiner—Richard L. Raymond
Attorney, Agent, or Firm—Edward J. Whitfield

[57] ABSTRACT

The invention relates to herbicidally active 3-oxadiazolyl-2-imidazolidinone derivatives, including herbicidal formulation and the use thereof to control the growth of noxious plants, i.e., weeds.

4 Claims, No Drawings

HERBICIDALLY ACTIVE 3-OXADIAZOLYL-2-IMIDAZOLIDINONES

FIELD OF THE INVENTION

This invention relates to certain 3-(5- or 3-substituted-1,2,4-oxadiazol-3-or -5-yl)-1-substituted-4-substituted amino-2-imidazolidinones having herbicidal activity and the use thereof to control the growth of noxious plants, i.e., weeds.

DESCRIPTION OF THE INVENTION

This invention provides herbicidally active 3-(5- or 3-substituted-1,2,4-oxadiazol-3- or -5-yl)-1-substituted-4- and/or 5-substituted amino-2-imidazolidinone compounds represented by the Formula I:

$$A-N\underset{R^2\ R^3}{\overset{O}{\underset{\|}{C}}}N-R^1$$

when A is $$R-\underset{O-N}{\overset{N}{\diagup}}\quad \text{or}\quad R-\underset{N-O}{\overset{N}{\diagup}}$$

when R is selected from up to $C_6$ alkyl, haloalkyl or cycloalkyl, up to $C_5$ alkenyl or alkynyl, $-R^4-O-R^5$ or $R^4-S-R^5$ wherein $R^4$ is up to $C_6$ alkylene and $R^5$ is up to $C_6$ alkyl or phenyl or benzyl;
$R^1$ is up to $C_3$ alkyl or allyl
$R^2$ and $R^3$ are selected from hydrogen, hydroxy or $$R^6-\overset{|}{N}-(CH_2)_n-OR^7$$

with the proviso that one of $R^2$ or $R^3$ must be $$R^6-\overset{|}{N}-(CH_2)_n-OR^7$$

wherein:
$R^6$ is hydrogen or up to $C_6$ alkyl, haloalkyl, alkoxy or alkoxylalkyl or acyl;
$R^7$ is hydrogen, up to $C_6$ alkyl, alkylcarbonyl or amino carbonyl; and
n is 2, 3 or 4.

Although any compound within the scope of Formula I is believed to have herbicidal activity, preferred compounds are those wherein R is lower alkyl, especially tertiary butyl, $R^1$ is alkyl, especially methyl and $R^2$ is $$R^6-\overset{|}{N}-(CH_2)_n-OR^7.$$

The compounds of this invention can be readily synthesized using known starting materials, such as the oxadiazolyl-imidazolidinone compounds described in U.S. Pat. No. 4,426,527 and using techniques known to the art. For example, certain of the compounds of this invention may be prepared by reacting an oxadiazolyl-4-hydroxy-2-imidazolidinone compound of the Formula II:

$$A-N\underset{OH}{\overset{O}{\underset{\|}{C}}}N-R^1$$

when A and $R^1$ are as previously defined with a suitably substituted amine of the Formula III:

$$HN\underset{(CH_2)_n-OR^7}{\overset{R^6}{\diagup}}$$

wherein $R^6$, $R^7$ and n are as previously defined. The reaction is typically conducted in an inert organic solvent medium at up to reflux temperature and usually in the presence of a strong mineral or organic acid, e.g. p-toluenesulfonic acid.

The following examples are illustrative of the preparation of certain specific compounds of this invention.

EXAMPLE I

Preparation of:
3-[5-(t-butyl)-1,2,4-oxadiazol-3-yl]-1-methyl-4-[N-(2-hydroxyethyl)]amino-2-imidazolidinone To a 50 milliliter flask provided with a Dean-Stark trap, a magnetic stirring bar and a reflux condenser were charged 2.40 grams (0.01 mole) of 3-[5-(t-butyl)-1,2,4-oxadiazol-3-yl]-1-methyl-4-hydroxy-2-imidazolidinone, 0.2 gram of p-toluenesulfonic acid, 10 milliliters of dry toluene and 0.92 gram (0.015 mole) of ethanolamine. The resulting clear, colorless solution was heated to reflux and maintained at reflux for 3 hours at which time TLC analysis indicated complete consumption of starting material. The reaction mixture was cooled to room temperature, diluted with 100 milliliters of ethyl acetate and washed consecutively with 100 milliliter portions of saturated aqueous sodium bicarbonate and saturated aqueous sodium chloride. The organic layer was drawn-off, dried over anhydrous sodium sulfate, filtered and concentrated in vacuo affording 1.29 grams of a golden oil confirmed by NMR analysis as the desired product.

EXAMPLE II

Preparation of:
3-[5-(t-butyl)-1,2,4-oxadiazol-3-yl]-1-methyl-4-[N-(2-methoxyethyl)]amino-2-imidazolidinone To 50 milliliter flask provided with a Dean-Stark trap, a magnetic stirring bar and a reflux condenser were charged 2.40 grams (0.01 mole) of 3-[5-(t-butyl)-1,2,4-oxadiazol-3-yl]-1-methyl-4-hydroxy-2-imidazolidinone, 0.1 gram of p-toluenesulfonic acid and, 10 milliliters of dry toluene. To this white suspension was added 1.12 grams (0.015 mole) of 2-methoxyethyl amine resulting in a pale yellow solution. The reaction mixture was heated to 70° C. via a heating mantle and maintained at 70° C. for 48 hours, at which time TLC analysis indicated complete conversion of starting material. The reaction mixture was cooled to room temperature, transferred to a separatory funnel, diluted with 100 milliliters of ethyl acetate and washed consecutively with 100 milliliter portions of saturated aqueous sodium bicarbonate and saturated aqueous sodium chloride. The organic layer was drawn-off, dried over anhydrous magnesium sulfate, filtered and concentrated in vacuo affording 2.28 grams of a golden oil confirmed by NMR analysis as the desired product.

Although the invention has been illustrated by the foregoing Examples with regard to the preparation of certain compounds within the scope of Formula I, it is to be understood that other compounds within the scope of Formula I may readily be prepared by those skilled in the art simply by varying the choice of starting materials and using the same or similar techniques.

Weed control in accordance with this invention is effected by applying to the soil prior to emergence of weeds therefrom or to the plant surfaces subsequent to emergence from the soil, a herbicidally effective amount of a compound of this invention. It is, of course, to be understood that the term "a compound of this invention" also includes mixtures of such compounds or a formulation containing a compound or mixture of compounds of this invention.

The term "herbicidally effective amount" is that amount of a compound of this invention required to so injure or damage weeds such that the weeds are incapable of recovering following application while not causing substantial injury to any valuable crop amongst which the weeds might be growing. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as one or less pound per acre of a compound of this invention would be expected to provide satisfactory weed control, although in some instances application rates in excess of one pound per acre, e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.01 to 2.0 pounds per acre.

Of course, a compound of this invention can be formulated according to routine methods with any of several known and commonly used herbicidal diluents, adjuvants and carriers. The formulations can contain liquid carriers and adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America*, may be used in combination with a compound or compounds of the invention. Typically such formulations will contain from about 5 to about 95 percent by weight of a compound of this invention.

The herbicidal formulations contemplated herein can be applied by any of several method known to the art. Generally, the formulation will be surfaced applied as an aqueous spray. Such application can be carried out by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention have been found effective for preemergence control of both broadleaf and grassy weeds, and postemergence control of grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curly dock, field chickweed, dandelion, Russian knapweed aster, horsetail, ironweed, sesbania, cattail, wintercress, horsenettle, nutsedge, milkweed, sicklepod, and the like.

The compounds prepared as described in the Examples were individually tested for herbicidal efficacy, against a variety of broadleaf and grassy weed species, under controlled laboratory conditions of light, humidity and temperature. Solvent solutions of said compounds were applied, both preemergence and postemergence, to test flats containing the various weed species, and herbicidal efficacy was determined by periodic visual inspection, after application of the compounds. Herbicidal efficacy was determined on a Numerical Injury Rating (NIR) scale of from 0 (no injury) to 10 (all plants dead). A NIR rating of 7-9 indicates severe injury; a NIR rating of 4-6 indicates moderate injury, i.e., plant growth is reduced to the extent that normal growth would be expected only under ideal conditions; and a NIR rating of 1-3 indicates slight injury.

The following table gives the average preemergence and postemergence NIR determined for each of the compounds prepared as described in Examples I and II on the broadleaf (BL) and grassy (GR) weed species to which the compounds were applied. The compound of Example I was applied at a rate of 1.0 pound per acre, the compound of Example II was applied at a rate of 0.5 pound per acre and the NIR was determined three weeks subsequent to application.

|  | I | II |
|---|---|---|
| Pre-BL | 9.8 | 9.7 |
| Pre-GR | 9.8 | 9.8 |
| Post-BL | 7.7 | 8.0 |
| Post-GR | 1.5 | 2.5 |

The broadleaf weeds used in the screening tests were coffeeweed, jimsonweed, tall morningglory, wild mustard, teaweed and velvetleaf. The grassy weeds used in the screening tests were barnyardgrass, large crabgrass, Johnsongrass, wild oats and yellow foxtail.

As the above test results indicate, the compounds of the invention are very effective for controlling broadleaf and grassy weeds when used preemergence and broadleaf weeds when used postemergence. Also, the relatively low level of postemergence activity exhibited against grassy weeds is advantageous since the invention compounds could be used for selective postemergence control of broadleaf weeds growing amongst a grassy or cereal crop such as, for example, wheat, oats, barley or rice without causing substantial harm to the crop.

Although the invention has been described in considerable detail by the foregoing, it is to be understood that many variations may be made therein by those skilled in the art without departing from the spirit and scope thereof as defined by the appended claims.

We claim:

1. A compound represented by the formula:

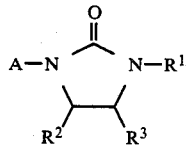

when A is

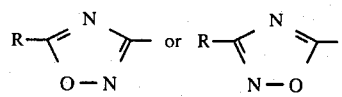

when R is selected from up to $C_6$ alkyl, haloalkyl or cycloalkyl, up to $C_5$ alkenyl or alkynyl, $-R^4-O-R^5$ or $R^4-S-R^5$ wherein $R^4$ is up to $C_6$ alkylene and $R^5$ is up to $C_6$ alkyl or phenyl or benzyl;

$R^1$ is up to $C_3$ alkyl or allyl $R^2$ and $R^3$ are selected from hydrogen, hydroxy or

with the proviso that one of $R^2$ or $R^3$ must be

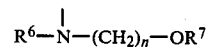

wherein:

$R^6$ is hydrogen or up to $C_6$ alkyl, haloalkyl, alkoxy or alkoxylalkyl or acyl;

$R^7$ is hydrogen, up to $C_6$ alkyl, alkylcarbonyl or amino carbonyl; and n is 2, 3 or 4.

2. A compound of claim 1 selected from: 3-[5-(t-butyl)-1,2,4-oxadiazol-3yl]-1-methyl-4-[N-(2-hydroxyethyl)]amino-2-imidazolidinone and 3-[5-(t-butyl)-1,2,4-oxadiazol-3-yl]-1-methyl-4-[N-(2-methoxyethyl)]amino-2-imidazolidinone.

3. A herbicidal formulation containing an agronomically acceptable carrier and a compound or mixture of compounds defined in claim 1.

4. In a method of controlling weeds wherein a herbicidally effective amount of herbicide is applied to a growth medium prior to emergence of weeds therefrom or to the weeds subsequent to their emergence from the growth medium, the improvement residing in using as the herbicide a compound or mixture of compounds defined in claim 1.

* * * * *